United States Patent [19]

Koenig et al.

[11] Patent Number: 4,775,673
[45] Date of Patent: Oct. 4, 1988

[54] SUBSTITUTED ACYLPIPERAZINOQUINAZOLINES AND PHARMACEUTICAL COMPOSITIONS CONTAINING SAME

[75] Inventors: Jan Koenig; Miroslav Rajsner; Vaclav Trcka; Sverluse Macova, all of Prague, Czechoslovakia

[73] Assignee: SPOFA, spojene podniky pro zdravotnickou vyrobu, Prague,

[21] Appl. No.: 851,339

[22] Filed: Apr. 14, 1986

Related U.S. Application Data

[63] Continuation-in-part of Ser. No. 616,542, Jun. 1, 1984, abandoned.

[30] Foreign Application Priority Data

Jun. 1, 1983 [CS] Czechoslovakia ............... 3905-83

[51] Int. Cl.$^4$ .................. A61K 31/505; C07D 403/04
[52] U.S. Cl. .................... 514/254; 544/291; 544/293; 544/386; 544/391
[58] Field of Search ................ 544/291; 514/254

[56] References Cited

U.S. PATENT DOCUMENTS

| | | | |
|---|---|---|---|
| 3,511,836 | 5/1970 | Hess | 544/291 |
| 3,574,212 | 4/1971 | Hess | 544/291 |
| 4,189,484 | 2/1980 | Mizogami et al. | 544/291 |
| 4,287,341 | 9/1981 | Hess et al. | 544/291 |
| 4,309,541 | 1/1982 | Werner | 544/291 |
| 4,377,581 | 3/1983 | Hess et al. | 544/291 |
| 4,426,382 | 1/1984 | Sato et al. | 544/291 |
| 4,440,769 | 4/1984 | DeBermardis et al. | 544/291 |
| 4,495,188 | 1/1985 | Sato et al. | 544/291 |

FOREIGN PATENT DOCUMENTS 2142625A 1/1985 United Kingdom ............... 544/291

Primary Examiner—Glennon H. Hollrah
Assistant Examiner—James H. Turnipseed
Attorney, Agent, or Firm—Klein & Vibber

[57] ABSTRACT

Substituted acylpiperazinoquinazolines of formula I

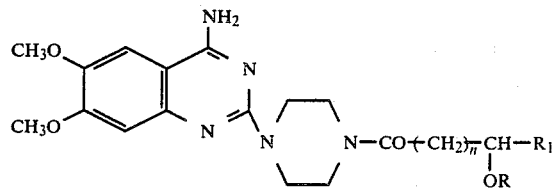

wherein n is 0 or 1, R represents an alkyl group with 1 to 4 carbon atoms or a benzyl group, and $R_1$ is a hydrogen atom, a methyl group or a phenyl group. Addition salts of these compounds with inorganic and organic acids are also disclosed. The compounds possess a significant antihypertensive activity. They can be prepared by the reaction of 2-halogeno quinazoline derivatives with the corresponding acylpiperazines, followed (if required) by neutralization of the respective base with a suitable acid to form its pharmaceutically convenient addition salt.

The acid addition salts, especially hydrochlorides, are readily soluble in water and give stable, almost neutral aqueous solutions which can be used in parenteral (injectable) and peroral medicinal dosage forms.

13 Claims, No Drawings

SUBSTITUTED ACYLPIPERAZINOQUINAZOLINES AND PHARMACEUTICAL COMPOSITIONS CONTAINING SAME

This application is a continuation-in-part of application Ser. No. 616,542 filed on June 1, 1984 now abandoned.

This invention relates to substituted acylpiperazinoquinazolines of formula I:

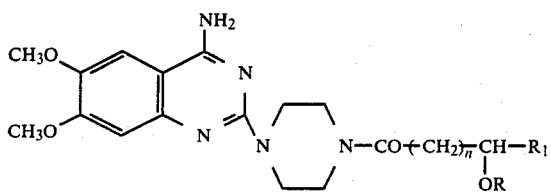

wherein n is 0 or 1, R represents an alkyl with 1 to 4 carbon atoms or a benzyl group and $R_1$ stands for a hydrogen atom, a methyl, or a phenyl group, as well as the addition salts of these compounds with inorganic or organic acids. The invention also relates to a process for the preparation of these compounds and to pharmaceutical compositions containing them.

In the art, 2-piperazino-4-amino-6,7-dimethoxyquinazoline compounds are known, and have been reported to possess antihypertensive activity. Prazosin, 1-(4-amino-6,7-dimethyoxy2-quinazolinyl)-4-(2-furoyl) piperazine hydrochloride (U.S. Pat. No. 3,511,836) has been used for many years in the therapy of hypertension. Prazosin reduces blood pressure by blocking the post-synaptic alpha$_1$-adrenergic receptors, and is a highly efficient antihypertensive compound. However, it shares a common disadvantage with related compounds in that it is only slightly soluble in water. This renders parenteral administration almost impossible, and yet such administration is frequently desired, because it provides for rapid onset of the therapeutic effect.

This disadvantage has been overcome by novel compounds of the present invention. Substituted acylpiperazinoquinazolines of formula I, in the form of their acid addition salts, and especially the respective hydrochlorides, are readily soluble in water and give stable, almost neutral aqueous solutions. The increased solubility of the present hydrochloride compounds over prazosin, which is also a hydrochloride, results from the acyl substitution of the piperazino nitrogen.

Of particular interest in this respect are the compounds of formula I above. The hydrochlorides of these compounds afford up to more than 15% aqueous solutions. In pharmacological tests on DOCA-hypertensive rats, normotensive monkeys, and rabbits, these particularly advantageous compounds demonstrated a markedly pronounced hypotensive effect, both on peroral and intravenous administration. In addition, the compounds of formula I are extremely non-toxic. In acute toxicity assays, their $LD_{50}$ values in mice are within a range of 1.3 to more than 4 g/kg p.o. and 80 to 360 mg/kg i.v.

A typical, highly advantageous compound of the invention is the corresponding 2-methyloxypropionyl derivative of formula I, in which n is 0 and both R and $R_1$ are methyl groups. In nonanesthesized (conscious) DOCA-hypertensive rats, this compound in an oral dose of 1 mg/kg elicits a blood pressure reduction of 20%. A dramatic reduction in blood pressure, as much as 40–50%, is observed in the same animals at a dose of 10 mg/kg p.o. Similarly, in non-anesthesized normotensive monkeys (Macaca mulatta), a dose of 3 mg/kg p.o. reduces the blood pressure by 20%. A dose of 25 mg/kg p.o. reduces blood pressure by 35 to 50% for a period of 7 to 9 hours. An intravenous administration of 2.5 mg/kg as a bolus to monkeys reduces blood pressure by 30 to 50% for 1 hour. A similar administration of 10 mg/kg i.v. elicits a blood pressure reduction of 50 to 70% for more then 7 hours. In rabbits anesthesized by pentobarbital, a dose of 25 mg/kg p.o. reduces blood pressure by 20 to 40% for a period of 4 to 5 hours. In non-anesthesized rabbits, a dose as low as 0.1 mg/kg i.v. elicits a transient but significant blood pressure reduction of almost 20%, shortly after administration. A dose of 1 mg/kg i.v. reduces the blood pressure by 20 to 30% for a period of more than 8 hours.

The 2-methoxypropionyl derivative of the present invention is extremely low in toxicity. In mice, a dose of 4 g/kg p.o. does not produce any toxic symptoms. The intravenous $LD_{50}$ in mice is 360 mg/kg, in rats 440 mg/kg.

The results of pharmacological tests, as summarized herein, indicate that the compounds of the present invention, especially in the form of their appropriate acid addition salts, are useful in the treatment of hypertonia and related cardiac insufficiencies in mammals.

The acylpiperazinoquinazoline compounds of formula I may be prepared as follows: A quinazoline derivative of formula II

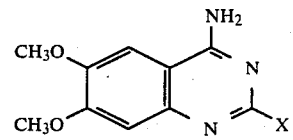

wherein X designates a reactive substituent, preferably a halogen atom or a methylthio group, is reacted in an inert organic solvent with an acylpiperazine of formula III,

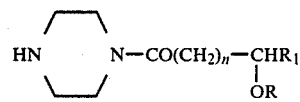

wherein n, R and $R_1$ have the same meaning as in the formula I. Subsequent isolation of the product is in the form of a base or an acid addition salt.

A preferable procedure consists in the reaction of acylpiperazines with 2-chloro-4-amino-6,7-dimethoxyquinazoline (U.S. Pat. No. 3,511,836). The reaction is advantageously conducted in butanol or isoamylalcohol at the boiling temperature of the reaction mixture and requires a reaction time of approximately 4 to 10 hours. On cooling, the crude hydrochloride product crystallizes and is collected on a filter. The obtained material can be purified by crystallization from a lower alkanol, such as methanol or aqueous ethanol, with or without the addition of ether.

The resulting hydrochlorides of the compounds of formula I can be converted into their respective bases by adjusting the aqueous solutions or suspensions to alkaline pH, with, for example, an aqueous sodium hydroxide solution. The basic products are isolated by extraction into a suitable organic solvent immiscible with water, such as chloroform with subsequent evaporation of the solvent. The bases obtained can be crystallized in a suitable solvent, such as ethanol. Neutralization with appropriate inorganic or organic acids in an anhydrous medium or in aqueous methanol or ethanol results in the corresponding acid addition salts.

Preferable addition salts of the compounds of formula I are their hydrochlorides, which are readily soluble in water and which provide a stable, almost neutral aqueous solution convenient for use in the formulation of parenteral (injectable) and peroral medicinal dosage forms. These can comprise a dosage unit substantially from 1 to 100 mg of a substituted acylpiperazinoquinazoline compound of the invention, in addition to common pharmaceutical auxiliaries, carriers, and/or excipients.

The intermediary acylpiperazines of formula III are also noel compounds. They are prepared by acylation of piperazine with known acylchlorides of formula IV,

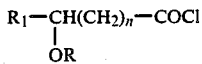

in which n, R and $R_1$ have the same meaning as in formula I. The acylation is preferably carried out in acetic acid, which suppresses the ditopic acylation of piperazine under the formation of undesired N,N'-diacylpiperazines, at a temperature of approximately 15° C. The acylpiperazines of formula III are isolated by dilution of the reaction mixture with water, if necessary following removal of the excess acetic acid by distillation. The solution is then adjusted to alkaline pH with aqueous sodium hydroxide, followed by repeated extraction with chloroform and evaporation of the solvent. The obtained crude bases of formula III can be purified either by distillation under reduced pressure or by conversion into a readily crystallizable addition salt, as with oxalic or fumaric acid. This step is followed by liberation of the base by alkaline treatment of an aqueous solution of the salt.

Further particulars of the preparation of the title compounds and the required new intermediates are described in the following examples, which are presented for purposes of exposition only and which do not serve to limit or restrict the scope of the invention.

EXAMPLE 1

1-(4-amino-6,7-dimethoxy-2-quinazolinyl)-4-(2-methoxyproprionyl)piperazine

A mixture of 1-(2-methoxypropionyl)piperazine (13.3 g) and 2-chloro-4-amino-6,7-dimethoxyquinazoline (15.5 g) in 160 ml of butanol is refluxed with stirring for 6 hours. On cooling, the reaction mixture is allowed to crystallize at room temperature for 16 hours. The crude product is collected on a filter and washed with 30 ml of ethanol. The yield is 23 g (86.6%) of the title compound in the form of hydrochloride, which melts at 280°–283° C. with decomposition. Another crystallization from 95% ethanol yields the corresponding hydrochloride monohydrate, melting at 238°–240° C. with decomposition. The title base is obtained by treatment of an aqueous solution of the hydrochloride with sodium hydroxide, subsequent extraction with chloroform and evaporation of the solvent. On crystallization from ethanol, the pure base melts at 219°–219.5° C.

The following acylpiperazinoquinazolines are prepared in a similar manner.

(a) 1-(4-amino-6,7-dimethoxy-2-quinazolinyl)-4-(2-ethoxypropionyl) piperazine, the hydrochloride of which crystallizes from methanol in the form of a monohydrate, m.p. 267°–270° C. with decomposition.

(b) 1-(4-amino-6,7-dimethoxy-2-quinazolinyl)-4-(2-butoxypropionyl) piperazine, the hydrochloride of which crystallizes from a methanol-ether mixture as a dihydrate, m.p. 225°–227° C. with decomposition.

(c) 1-(4-amino-6,7-dimethoxy-2-quinazolinyl)-4-(2-benzyloxypropionyl) piperazine, the hydrochloride of which crystallizes from ethanol as a monohydrate, m.p. 200°–203° C. with decomposition.

(d) 1-(4-amino-6,7-dimethoxy-2-quinazolinyl)-4-methoxyacetyl piperazine, the hydrochloride of which crystallizes from ethanol as a monohydrate, m.p. 236°–239° C. with decomposition.

(e) 1-(4-amino-6,7-dimethoxy-2-quinazolinyl)-4-ethoxyacetylpiperazine, the hydrochloride of which crystallizes from methanol as a dihydrate, m.p. 252°–255° C. with decomposition.

(f) 1-(4-amino-6,7-dimethoxy-2-quinazolinyl)-4-(alphamethoxyphenylacetyl) piperazine, the hydrochloride of which crystallizes from an ethanol-ether mixture in the form of a sesquihydrate (with 1.5 molecules of water), m.p. 237°–240° C. with decomposition.

EXAMPLE 2

1-(4-amino-6,7-dimethoxy-2-quinazolinyl)-4-(3-methoxypropionyl) piperazine

A mixture of 1-(3-methoxypropionyl) piperazine (6.4 g) and 2-chloro-4-amino-6,7-dimethoxyquinazoline (8.9 g) in 100 ml of isoamylalchohol is refluxed with stirring for 6 hours. The reaction mixture is cooled at room temperature for 12 hours. The crystallized product is separated and wet recrystallized by dissolving in warm methanol, with the subsequent addition of ether to the beginning of turbidity. The yield is 13.4 g of the title compound in the form of a hydrochloride monohydrate, which melts at 268°–272° C. with decomposition. Another crystallization from a methanol-ether mixture yields the analytically pure product melting at 273°–278° C. with decomposition.

EXAMPLE 3

1-(2-methoxypropionyl) piperazine

A solution of piperazine hexahydrate (22 g) in 80 ml of acetic acid is treated dropwise under vigorous stirring with 2-methoxypropionylchloride (12.2 g). During this dropwise addition, the reaction mixture is cooled with water and ice to maintain its temperatures at 14°–16° C. The mixture is then brought slowly to room temperature, with continued stirring, and is thereafter allowed to stand for 12 hours. The mixture is then poured into 550 ml of water. The resulting solution is adjusted to pH 10 with 50% aqueous sodium hydroxide under water cooling. The precipitated sodium acetate is filtered off, washed with chloroform, and the aqueous filtrate is extracted three times with the same solvent. The combined carbonate and solvent is evaporated under reduced pressure on a vacuum rotary evaporator. The resulting crude title base is purified by distillation under reduced pressure to yield 76.7 g (64.6%) of the base, boiling at 118°–121° C. under a pressure of 133 Pa. A sample is neutralized with a solution of ethanolic fumaric acid to yield the crystalline hydrogen fumarate which, on crystallization from ethanol, melts at 159°–161° C. The obtained hydrogen fumarate yields the pure base by treating its aqueous solution with sodium hydroxide, and by subsequent extraction with chloroform and evaporation of the solvent.

The following acylpiperazines are obtained in a similar manner. Unless otherwise stated, the acid addition salts were crystallized from a methanol-ether mixture and melted with decomposition.

(a) 1-(2-ethoxypropionyl) piperazine, oxalate m.p. 206°–212° C.

(b) 1-(2-butoxypropionyl) piperazine, hydrogenoxalate m.p. 163° C.

(c) 1-(2-benzyloxypropionyl) piperazine, oxalate m.p. 185°–187° C.

(d) 1-methoxyacetyl piperazine, oxalate m.p. 175°–177.5° C. (ethanol), (e) 1-ethoxyacetyl piperazine, oxalate m.p. 206°–212.5° C.

(f) 1-(alpha-methoxyphenylacetyl) piperazine, oxalate m.p. 140°–142° C.

(g) 1-(3-methoxypropionyl) piperazine, oxalate m.p. 215°–220° C.

We claim:

1. Substituted acylpiperazinoquinazolines of formula I

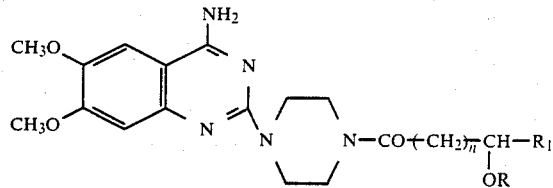

wherein n is 0 or 1, R is selected from the group consisting of an alkyl group with 1–4 carbon atoms and a benzyl group, and $R_1$ is selected from the group consisting of a hydrogen atom, a methyl group, and a phenyl group.

2. An acid addition salt of a compound of claim 1.

3. A hydrochloride of a compound of claim 1.

4. 1-(4-amino-6,7-dimethoxy-2-quinazolinyl)-4-(2-methoxypropionyl) piperazine.

5. 1-(4-amino-6,7-dimethoxy-2-quinazolinyl)-4-(2-ethoxypropionyl) piperazine.

6. 1-(4-amino-6,7-dimethoxy-2-quinazolinyl)-4-(2-butoxypropionyl) piperazine.

7. 1-(4-amino-6,7-dimethoxy-2-quinazolinyl)-4-(2-benzyloxypropionyl) piperazine.

8. 1-(4-amino-6,7-dimethoxy-2-quinazolinyl)-4-methoxyacetyl piperazine.

9. 1-(4-amino-6,7-dimethoxy-2-quinazolinyl)-4-ethoxyacetyl piperazine.

10. 1-(4-amino-6,7-dimethoxy-2-quinazolinyl)-4-(alphamethoxyphenylacetyl) piperazine.

11. 1-(4-amino-6,7-dimethoxy-2-quinazolinyl)-4-(alphamethoxypropionyl) piperazine.

12. The hydrochloride of the compounds of claims 4, 5, 6, 7, 8, 9, 10 or 11.

13. Pharmaceutical compositions comprising a substituted acylpiperazinoquinazoline whether or not in the form of its acid addition salt, as claimed in claims 1 or 2, wherein the claimed compounds are combined with a pharmaceutical excipient.

* * * * *